United States Patent [19]

Horvath

[11] Patent Number: 4,923,477
[45] Date of Patent: May 8, 1990

[54] PROSTHESIS DRIVE

[75] Inventor: Eduard Horvath, Vienna, Austria

[73] Assignee: Otto Bock Orthopädische Industrie Besitz- Und Verwaltungs-KG, Duderstadt, Fed. Rep. of Germany

[21] Appl. No.: 381,609

[22] Filed: Jul. 18, 1989

[30] Foreign Application Priority Data

Jul. 18, 1988 [AT] Austria ................................ 1842/88

[51] Int. Cl.$^5$ .............................................. A61F 2/66
[52] U.S. Cl. ......................................... 623/57; 623/63; 901/38
[58] Field of Search ........................ 623/63, 64, 65, 57; 901/31, 34, 38; 74/675, 665 D, 665 E

[56] References Cited

U.S. PATENT DOCUMENTS 4,598,942 7/1986 Shum et al. ............................. 901/31
4,696,501 9/1987 Webb ..................................... 901/34

FOREIGN PATENT DOCUMENTS 2121023 11/1972 Fed. Rep. of Germany .

Primary Examiner—Richard J. Apley
Assistant Examiner—David H. Willse
Attorney, Agent, or Firm—Herbert Dubno

[57] ABSTRACT

A prosthesis drive, especially for a hand prosthesis, can rapidly approach the grippers until resistance is sensed and then apply an increased force to the object. For this purpose, two electric motors drive selectively the respective planetary gearing in an arrangement in which the planet wheels of the two gearings engage a common gear between the sun and ring gear of one planetary gearing or the sun and ring gear of the other planetary gearing, the gearings being coaxial with one another and with the motors. A circuit responding to an increase in the current of the high speed motor above a threshold value is provided to control the switchover.

8 Claims, 3 Drawing Sheets

PROSTHESIS DRIVE

FIELD OF THE INVENTION

My present invention relates to a prosthesis drive and, more particularly, to a prosthesis drive which is particularly suited for incorporation into an artificial hand. e.g. the artificial hand of the concurrently filed copending application Ser. No. 07/381,604 (attorney's docket No. 17316) based upon Austrian Patent Application No. A 1841/88, filed July 18, 1988.

More particularly, the invention relates to a prosthesis drive having a planetary gear transmission and which has two inputs from respective motors and at least one output which is driven from one or both of the inputs through the planetary gearing. Specifically, the drive can be used for the movement of grippers to generate a natural gripper movement for artificial hands, for example, which can have two grippers, one for a thumb and another for a middle finger and an index finger and which enables relatively rapid hand closing movement to be generated with minimum torque and, as soon as resistance is encountered, with a greater torque and reduced speed to engage an object between the grippers. Grippers and a hand with which the drive of the invention can be used are described in the aforementioned copending application.

Generally, prosthesis drives have included a motor and a transmission for reducing the speed of the output of the transmission by comparison with the speed at the input and enabling the generation of high torques. For the most part, however, such earlier transmissions cannot be used in an operating mode of the type described to accommodate a high-speed closure movement with low torque until the object is encountered and then a low speed high torque action so that the object can be reliably gripped, without complexities which have made earlier drives impractical, excessively large and excessively heavy.

OBJECTS OF THE INVENTION

It is, therefore, the principal object of the present invention to provide an improved prosthesis drive which can overcome the drawbacks of earlier drives, e.g. for artificial hands.

Another object of my invention is to provide an improved prosthesis drive which can effect a rapid closure movement of the grippers of an artificial hand prosthesis and then can be switched over to operate at low speed and with high torque for reliable gripping of an object, thereby providing a more natural gripping action for the artificial hand.

It is also an object of this invention to provide a drive of the type described which is highly compact and, in particular, can be readily built into a part of the prosthesis so as to avoid an anaesthetic appearance thereof.

Yet another object of this invention is to provide a prosthesis drive which has a minimum weight and yet can provide the favorable action sought above.

SUMMARY OF THE INVENTION

These objects are attained, in accordance with the invention, by providing three internally toothed mutually coaxial ring gears including an intermediate or inner ring gear and two outer ring gears having different numbers of teeth and with which at least two planet gears are engageable, each of which also engages an intermediate one of the ring gears, but meshes only with a respective one of the two outer ring gears. The planetary gearings are driven alternatively by respective externally toothed inner sun gears connected to respective motors. As a consequence of the alternative drive of these sun gears, the output will derive from one or the other of the inputs and hence from one or the other of the motors.

With this arrangement, the grippers can be displaced in an optimal manner, rapidly into the gripping position and then more slowly with the requisite high gripping force. The fingers and thumb forming the grippers can be connected to the output side of the transmission or drive. The difference in tooth numbers of the internally toothed range gears can be selected at will to provide the respective gear ratios with which the two motors deliver torque to the output.

According to the invention, therefore, a prosthesis drive can comprise:

a first and a second drive motors;

three mutually coaxial first gears disposed in succession along a common axis and including a pair of axially outer gears and an inner gear between the outer gears;

two second gears spaced along the axis, coaxial with the first gears and each defining an annular space with a respective one of the outer gears;

a respective sets of planet wheels in each of the annular spaces meshing with one of the second gears and the respective first gear, whereby each of the first gears, a respective set of the planet wheels and a respective one of the second gears forms a respective planetary gearing, the planet wheels of both the sets meshing with the inner gear;

means for coupling each of the first and second drive motors with one of the first and second gears of a respective one of the planetary gearings for alternative operation of the drive by the first and second motors, the first and second drive motors being disposed at opposite axial sides of the first gears; and means for connecting at least one of the others of the first and second gears of the planetary gearings not coupled to the motors to a member of a prosthesis movable relative to another member of the prosthesis.

According to a feature of the invention, at least one of the planet wheels and preferably both sets of planet wheels are provided in a stepped configuration, i.e. with two stages. This provides an especially compact arrangement of the transmission. A variation in the transmission ratio can be achieved by corresponding selection of the steps and with good efficiency. It is, however, also possible to provide the planet wheels so that they are single stage, i.e. the diameters of the planet wheels where they engage two of the range gears, do not differ from one another.

According to another feature of the invention, the inner or central internally toothed ring gear has a pitch circle diameter which corresponds to the pitch circle diameter of at least one of the outer ring gears disposed adjacent the inner ring gear. This embodiment simplifies fabrication of the transmission but reduces the operating efficiency thereof.

To achieve a desired ratio between the speeds of the two drive parts, one or more pretransmission stages may be provided between the respective drive motor and the sun gear or input element of the respective planetary gripping. The pretransmission gearings can also be planetary gearing drives, if desired.

For an automatic switchover from one motor to the other, I may provide an electronic switching circuit for the two motors and, specifically, a circuit which turns off one of the drive motors when a threshold value of a current drawn thereby is reached and simultaneously turns on the other drive motor.

While the sun and ring wheels of the transmission are coaxial and, in the preferred or best-mode embodiment, the motor shafts are coaxial with these wheels and one another, the motor shafts need not be coaxial with the transmission or even axially aligned with one another.

BRIEF DESCRIPTION OF THE DRAWING

The above objects, features and advantages of my invention will become more readily apparent from the following description, reference being made to the accompanying drawing in which.

SPECIFIC DESCRIPTION

Figure 1:
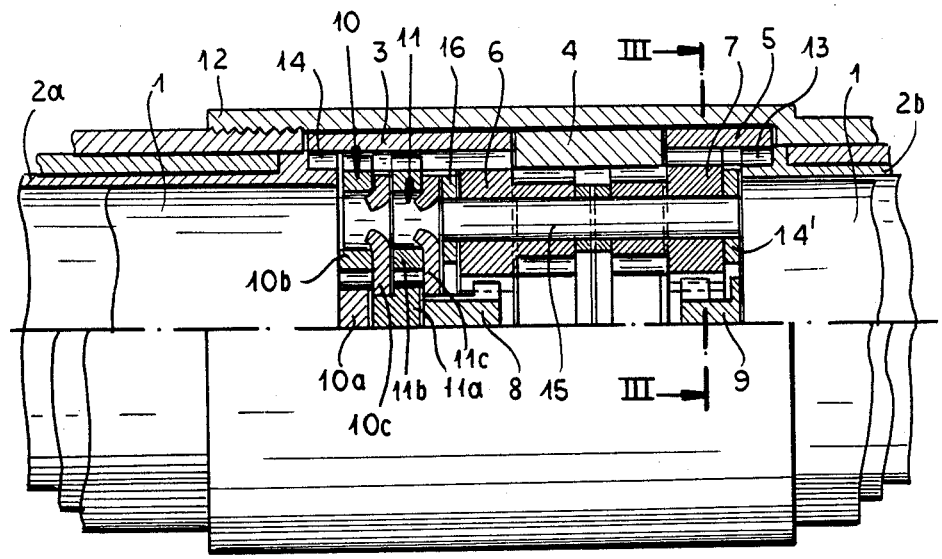
FIG. 1 is an axial section through a first embodiment of a prosthesis drive according to the invention.

In the drawing, two drive motors are represented at 1 and are disposed coaxial to one another. These motors may be miniature electric motors and can be fully received in the sleeve or housing of the transmission.

The transmission has a single output in the form of relative rotation which can be tapped at 2a and 2b to the relatively rotatable parts of the prosthesis. The output taps 2a and 2b may be sleeves which surround the drive motors 1. The drive tap 2b can be operatively coupled with the finger gripper, namely, the gripper formed by the index and middle fingers, of the prosthesis of the aforedescribed application, while the output tap 2a may be operatively connected with the gripper provided with the thumb of that artificial hand.

The planetary transmission can comprise three internally toothed outer ring gears 3, 4 and 5 with different tooth numbers. The ring gears 3, 4 and 5 are coaxially oriented.

The ring gears 3, 4 and 5 are in mesh with two sets of planet wheels 6, 7, each set of planet wheels meshing with the inner or intermediate ring gear 4 and one of the outer ring gears 3, 5 flanking the intermediate ring gear 4.

The planet wheels 6 and 7 are alternatively driven by respective externally toothed inner sun gears 8 and 9.

In the embodiment of FIG. 1, both planet wheels 6, 7 are formed as two-stage or stepped planet wheels. They, therefore, differ from the planet wheels 6', 7' of the embodiment of FIG. 2 where the prosthesis drive has two sets of planet wheels 6', 7' without steps. In this embodiment, the inner or central internally toothed ring gear 4' has a pitch diameter which corresponds to the pitch diameter of the two internally toothed ring gears 3 and/or 5 flanking and directly neighboring the intermediate ring gear 4'.

In the embodiment of FIG. 1, by contrast, the inner or intermediate internally toothed ring gear 4 has a pitch diameter which is less than the pitch diameters of the two internally toothed ring gears 3 and 5 flanking same.

Figure 2:
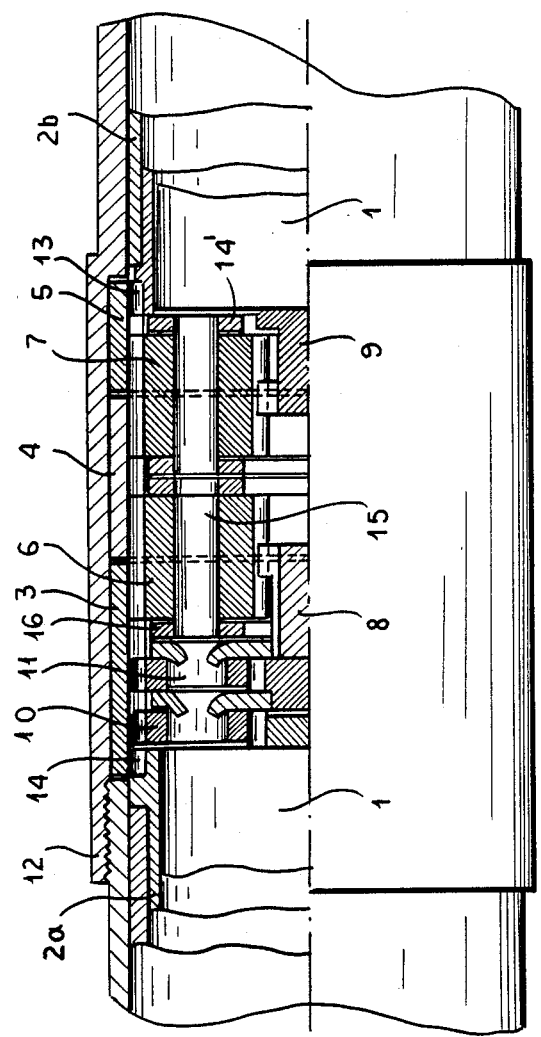
FIG. 2 is a section similar to FIG. 1 through a second embodiment.

In the embodiments of FIGS. 1 and 2, two preliminary transmission stages 10 and 11 are provided which coupled the left-hand motor 1, in each case, to the sun gear 8. For example, stage 10 is a planetary gear transmission which has a sun gear 10a driven by the left-hand motor 1 and meshing with planet gears 10b which, in turn, mesh with the ring gear 3. The planet carrier 10c of the planet gears 10b is connected to a sun gear 11a of the next stage. The sun gear 11a of stage 11, meshes with the planet gears 11b thereof, these planet gears also meshing with the ring gear 3.

The plant carrier 11c, however, meshes with the ring gear 8 previously mentioned. A similar construction is provided for the pretransmission stages 10 and 11 of the embodiment of FIG. 2.

The preliminary stages, while preferably in the form of planetary gearings, can also be other types of transmissions.

For the selective switching of the two motors 1, a preferably electronic circuit switching circuit can be provided and is described in greater detail below. This circuit can be embodied in a single printed circuit, chip or the like.

Upon attainment of a threshold value of the current in, for example, one of the drive motors, for example, the drive motor disposed at the right-hand end of the drive, the latter is brought to standstill and the other electric motor, in this case the left-hand electric motor, is switched on.

The planetary drive is received in a sleeve-like housing 12 which can represent the finger gripper or the thumb gripper of the aforementioned copending application. The output 2b is connected by a spline coupling 13 with the ring gear 5 while the output 2a is similarly connected via a spline coupling 14 with the ring gear 3.

As noted, the externally toothed sun gears 8 and 9 can either be directly connected with the respective motor or connected with the motor 1 via one or more pretransmission gearings 10, 11, etc..

Figure 3:
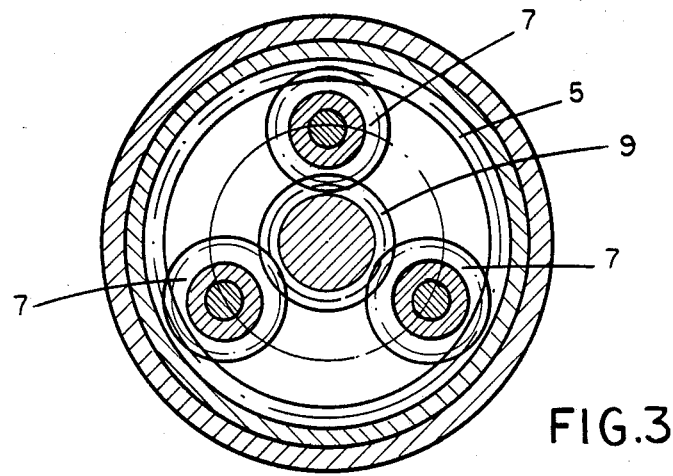
FIG. 3 is a section taken along the line III—III of FIG. 1.

As can be seen from FIG. 3, each set of planet wheels 6 or 7 can comprise three planet wheels. The planet wheels 7 are journaled in a cage or planet carrier 14' while the shafts 15 of the planet wheel 6 are journaled in a carrier 16.

The drive shown in FIGS. 1–3 functions, therefore, as follows:

If the right-hand motor is in operation at high speed, the gripper connected to the output 2a or 2b is rapidly driven in a closing direction. The second motor, here the left-hand motor, remains at standstill. As soon as an increased resistance is felt between the two grippers, the current drawn by the energized motor rises. the electronic threshold detector then switches over to the second electric motor, i.e. the left-hand motor, and holds the first motor at standstill. The limiting current of the left-hand motor thus determines the maximum holding force. Switchover of the closing action from one motor to the other can be accomplished with a hand-held switch or through skin or muscle sensors.

It is important, in accordance with the invention, that only one of the electric motors is placed in operation at any time while the other is held against rotation, i.e. prevented from running backwards. This can be accomplished by a unirotational lock preventing either motor from rotating in reverse.

Figure 4:
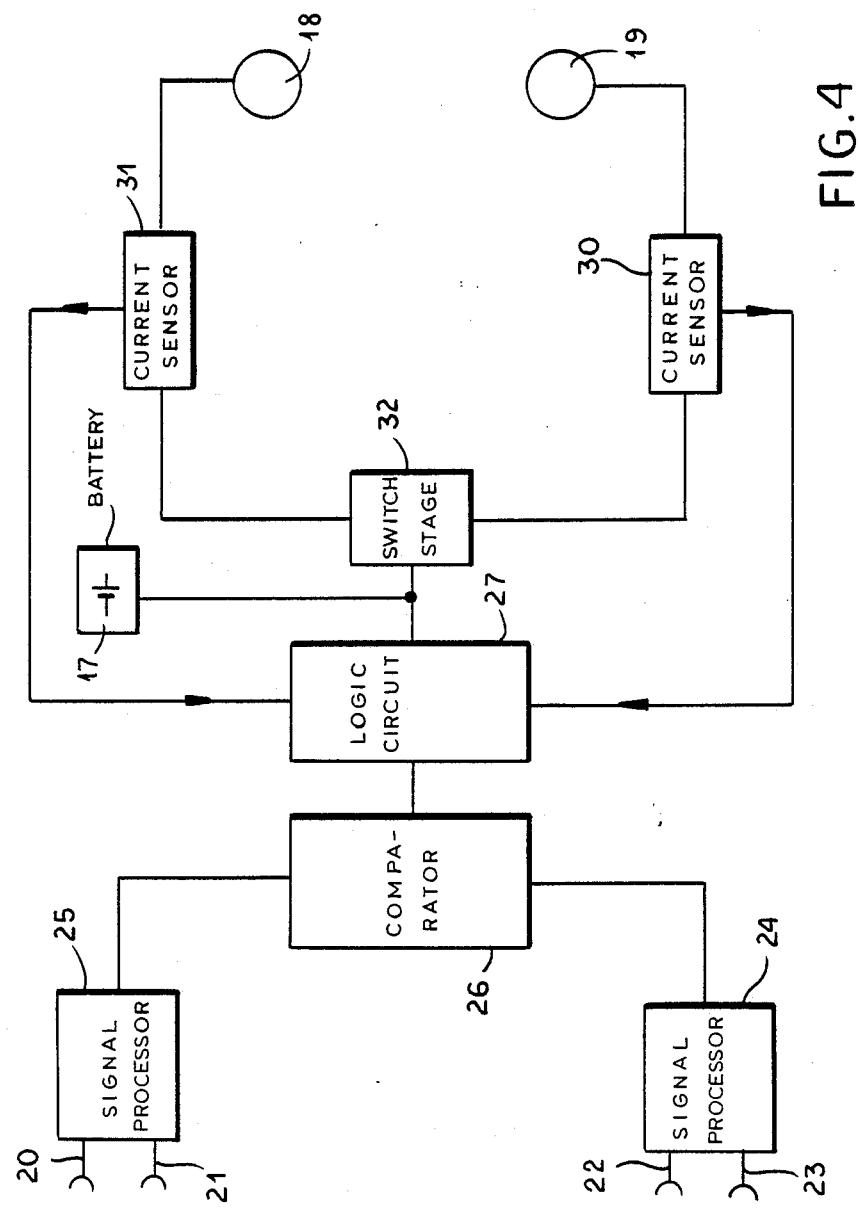
FIG. 4 is a block diagram of an electrical or an electronic circuit according to the invention for controlling the drive of FIG. 1 or FIG. 2.

The circuit used for controlling the drive of FIGS. 1–3, has been illustrated in FIG. 4.

This drive can include a battery 17 for supplying the current selectively to one or the other of the electronic motors 18 and 19 corresponding to the drive motors 1 previously described. Control signals are derived from skin electrodes 20, 21, 22 and 23. The control signals are amplified and rectified in signal processing stages 24 and 25 before being supplied to a comparator circuit 26. The output of the comparator 26 is applied to a logic circuit 27 to which current signals are fed back from current sensors 30 and 31 in the energization paths of the motors 18 and 19. The output of the logic circuit 27 is applied to a switching stage 32 which switches over the battery to the respective motor. The other motor, when unenergized, is blocked against rotation.

I claim:

1. A prosthesis drive, comprising:

a first and a second drive motor;

three mutually coaxial first gears disposed in succession along a common axis and including a pair of axially outer gears and an inner gear between said outer gears;

two second gears spaced along said axis, coaxial with said first gears and each defining an annular space with a respective one of said outer gears;

a respective set of planet wheels in each of said annular spaces meshing with one of said second gears and the respective first gear, each of the sets of planet wheels comprising at least one planet wheel, whereby each of said first gears, a respective set of said planet wheels and a respective one of said second gears forms a respective planetary gearing, said first wheels of both of said sets meshing with said inner gear;

means for coupling each of said first and second drive motors with one of said first and second gears of a respective one of said planetary gearings for alternative operation of the drive by said first and second motors, said first and second drive motors being disposed at opposite axial sides of said first gears; and means for connecting at least one of the others of the first and second gears of the planetary gearings not coupled to said motors to a member of a prosthesis movable relative to another member of the prosthesis.

2. The prosthesis drive defined in claim 1 wherein said first gears are internally toothed ring gears and said second gears are externally toothed sun gears, each of said sets of planet wheels having a respective planet carrier.

3. The prosthesis drive defined in claim 2 wherein the planet wheels of at least one of said sets are stepped with larger and smaller gear portions.

4. The prosthesis drive defined in claim 2 wherein said inner gear has a pitch circle diameter substantially coinciding with a pitch circle diameter of at least one of the outer first gears.

5. The prosthesis drive defined in claim 2 wherein said means for coupling includes at least one gear transmission interposed between one of said motors and a respective one of the first and second gears of the respective planetary gearing as a pretransmission stage.

6. The prosthesis drive defined in claim 5 wherein said pretransmission stage is a planetary gear transmission.

7. The prosthesis drive defined in claim 1, further comprising switch means connected with said motors and responsive to the development of a threshold current in one of said motors for electrically terminating drive of said one of said motors and electrically driving the other of said motors.

8. The prosthesis drive defined in claim 7 wherein said switch means is an electronic circuit.

* * * * *